(12) United States Patent
Ohki et al.

(10) Patent No.: US 6,371,111 B1
(45) Date of Patent: Apr. 16, 2002

(54) INHALATION TYPE DRUG DISPENSER

(75) Inventors: Hisatomo Ohki; Yoshiyuki Yazawa; Shigemi Nakamura; Kazunori Ishizeki, all of Gunma; Akira Yanagawa, Yokohama, all of (JP)

(73) Assignees: Unisia Jecs Corporation, Atsugi (JP); Dott Limited Co., Yokohama (JP)

( * ) Notice: Subject to any disclaimer, the term of this patent is extended or adjusted under 35 U.S.C. 154(b) by 0 days.

(21) Appl. No.: 09/623,478

(22) PCT Filed: Dec. 27, 1999

(86) PCT No.: PCT/JP99/07305

§ 371 Date: Jan. 13, 2000

§ 102(e) Date: Jan. 13, 2000

(87) PCT Pub. No.: WO00/44426

PCT Pub. Date: Aug. 3, 2000

(30) Foreign Application Priority Data

Jan. 27, 1999 (JP) .............................................. 11-19145

(51) Int. Cl.⁷ ........................ A61M 15/00; A61M 16/00; B05D 7/14; B05D 83/06
(52) U.S. Cl. ............................ 128/203.15; 128/203.12; 128/203.23; 604/58
(58) Field of Search ..................... 128/203.15, 203.19, 128/203.21, 205.21, 203.12, 203.23; 604/58

(56) References Cited

U.S. PATENT DOCUMENTS

| | | | | |
|---|---|---|---|---|
| 4,175,556 A | * | 11/1979 | Freezer | 128/198 |
| 4,668,218 A | * | 5/1987 | Virtanen | 604/58 |
| 4,841,964 A | * | 6/1989 | Hurka et al. | 128/203.15 |
| 5,176,132 A | * | 1/1993 | Drought et al. | 128/203.15 |
| 5,243,970 A | * | 9/1993 | Ambrosio et al. | 128/203.15 |
| 5,301,666 A | * | 4/1994 | Lerk et al. | 128/203.15 |
| 5,309,900 A | * | 5/1994 | Knoch et al. | 128/200.14 |
| 5,503,144 A | * | 4/1996 | Bacon | 128/203.15 |
| 5,619,985 A | | 4/1997 | Ohki et al. | 128/203.21 |
| 5,647,349 A | | 7/1997 | Ohki et al. | 128/203.15 |
| 5,699,789 A | * | 12/1997 | Hendricks | 128/203.15 |
| 5,715,811 A | | 2/1998 | Ohki et al. | 128/203.21 |
| 5,752,505 A | | 5/1998 | Ohki et al. | 128/203.15 |
| 5,810,004 A | | 9/1998 | Ohki et al. | 128/203.15 |
| 5,899,202 A | | 5/1999 | Ohki et al. | 128/203.22 |
| 5,901,703 A | | 5/1999 | Ohki et al. | 128/203.12 |
| 5,921,236 A | | 7/1999 | Ohki et al. | 128/203.15 |
| 5,989,217 A | | 11/1999 | Ohki et al. | 604/94 |
| 5,996,577 A | | 12/1999 | Ohki et al. | 128/203.15 |
| 6,116,237 A | * | 9/2000 | Schultz et al. | 128/203.15 |
| 6,142,145 A | * | 11/2000 | Dagsland et al. | 128/203.15 |
| 6,273,086 B1 | | 8/2001 | Ohki et al. | 128/203.21 |

FOREIGN PATENT DOCUMENTS

| | | |
|---|---|---|
| JP | 7-313599 | 12/1995 |
| JP | 8-89576 | 4/1996 |
| JP | 9-503928 | 4/1997 |
| WO | WO-90/15635 | * 12/1990 |
| WO | WO 95/03846 | 2/1995 |

* cited by examiner

*Primary Examiner*—John G. Weiss
*Assistant Examiner*—Darwin P. Erezo
(74) *Attorney, Agent, or Firm*—Foley & Lardner

(57) ABSTRACT

An inhalant medicator includes a medicator body 1 which is formed therein with a cylindrical fit hole 2, an inhalant port 3, an inflow air passageway 5, and an outflow air passageway 6, and a medical powder storage cylindrical member 8 which is installed or fitted into the cylindrical fit hole 2 in a manner so as to open or close the air passageways 5 and 6 with respect to a medical powder storage chamber 12. The inhalant medicator is constructed by two component parts, namely the medicator body 1 and the medical powder storage cylindrical member 8, thus ensuring simplified structure and reduced production costs. Additionally, powder-and-granular medicine or medical powder 16 is tightly encapsulated within the medical powder storage chamber 12 by means of the medical powder storage cylindrical member 8, thus preventing loss of flow of the medical powder 16.

11 Claims, 14 Drawing Sheets

INHALATION TYPE DRUG DISPENSER

TECHNICAL FIELD

The invention relates to an inhalant medicator suitable to prescribe granular or powdered medicines (medical powder) toward within lungs of a patient by way of breathing action of the patient.

BACKGROUND ART

Generally, there are two medications of prescribing a medicine toward within lungs of an asthmatic patient, that is, one being a medication that a medicine is inhaled by way of a liquid aerosol atomizer, and the other being an inhalation treatment that granular or powdered medicines (which will be hereinafter referred to as "medical powder") encapsulated in a capsule are inhaled.

Of these medications for an asthmatic patient, an inhalant medicator used for an inhalation treatment where encapsulated medical powder is inhaled, has been disclosed in Japanese Patent Provisional Publication No. 7-313599.

The inhalant medicator as disclosed in the above Japanese Patent Provisional Publication is generally comprised of a medicator body equipped at one axial end with a capsule housing hole and at the other axial end with an inhalant port, an inflow air passageway formed in the medicator body for flowing air into the capsule housing hole, an outflow air passageway formed in the medicator body for flowing medical powder stored in the capsule of the capsule housing hole together with air flown through the inflow air passageway into the inhalant port, pin insertion holes located at both sides of the capsule housing hole in the axial directions of the capsule housing hole and bored in the medicator body in such a manner as to extend in a radial direction of the medicator body for communicating each of the inflow and outflow air passageways, and a boring tool having pins insertable toward the capsule through the respective pin insertion holes for breaking through the capsule accommodated in the capsule housing hole.

In such inhalant medicators, the capsule is accommodated in the capsule housing hole, and holes, communicating the internal space of the capsule with each of the air passageways, are pricked or punched by means of the boring tool. Under this condition, the patient draws his or her breath while talking the inhalant port in his or her mouth, and thus air is flown from the atmospheric side through the inflow air passageway into the capsule. The air flow carries and discharges the medical powder stored in the capsule through the outflow air passageway into the inhalant port. In this manner, the medical powder flowing out of the capsule can be inhaled though the inhalant port into the lungs of the patient.

The conventional inhalant medicator described above, is constructed so that a capsule is inserted into a capsule housing hole of a medicator body, and the medical powder stored in the capsule is inhaled by pricking or punching holes in the capsules by way of a boring tool. For the reasons set forth above, there is the necessity for pin insertion holes and the boring tool. This increases the number of component parts, and induces a complicated structure. Thus, there are some problems, such as increased production costs and increased economical burden of a patient.

Also, in recent years, there are other problems, such as sanitary problems, and a throwaway type of medicator is desirable. In particular, in a case of a dose of medicine to be taken only once, a medicator is not used continuously. In this case, a new medicator is used only once for each medication. A so-called throwaway type of medicator exists. Therefore, people can think about the use of the conventional medicator as a throwaway type. However, for the reasons set out above, this medicator is not suitable to use as a throwaway type.

DISCLOSURE OF THE INVENTION

It is, therefore, in view of the previously-described disadvantages of the prior art, an object of the present invention to provide an inhalant medicator which is capable of reducing production costs by reducing the number of component parts and by simplifying its structure.

In order to accomplish the aforementioned and other objects, according to the invention, an inhalant medicator comprises a medicator body formed with a cylindrical fit hole opening at one axial end and formed at the other axial end with an inhalant port, an inflow air passageway formed in the medicator body for supplying air into the cylindrical fit hole, an outflow air passageway formed in the medicator body for discharging air from the cylindrical fit hole into the inhalant port, and a medical powder storage cylindrical member having a cylindrical portion defining therein a medical powder storage hole whose internal space stores a medical powder and capable of opening and closing each of the inflow air passageway and the outflow air passageway with respect to the medical powder storage hole by external operation.

In the inhalant medicator as constructed above, under a condition where the inflow air passageway and the outflow air passageway are closed with respect to the medical powder storage hole by means of the medical powder storage cylindrical member, it is possible to prevent the medical powder stored in the medical powder storage hole from flowing to the outside via the air passageways. On the other hand, when the medical powder has to be inhaled, the inflow air passageway and the outflow air passageway are communicated with the medical powder storage hole by operating the medical powder storage cylindrical member. Under these conditions, the patient draws his or her breath while taking the inhalant port in his or her mouse, atmosphere flown into the inflow air passageway flows into the medical powder storage hole, taking the form of air flow. As a result of this, the medical powder in the medical powder storage hole can be atomized. Thus, in a blended condition of the medical powder with air flow, the mixture of the incoming air and medical powder passes through the outflow air passageway and then flows towards within the inhalant port, and then the mixture is inhaled through the inhalant port into lungs of the patient.

The inhalant medicator of the invention is constructed by two component parts, namely the medicator body and the medical powder storage cylindrical member, and also it is possible to open and close each of the air passageways with respect to the medical powder storage hole by means of the medical powder storage cylindrical member, thus ensuring a simple structure of the medicator. This reduces production costs. Additionally, even when the medical powder storage hole is filled with granular or powdered medicines in advance, it is possible to prevent the medical powder stored in the medical powder storage hole from flowing to the outside.

According to the invention, at least one medical powder diffusion chamber is formed in the medicator body and located between the cylindrical fit hole and the inhalant port for diffusing the medical powder flowing out of the outflow air passageway.

In the inhalant medicator as constructed above, when the patient draws his or her breath while taking the inhalant port in his or her mouth, the medical powder flowing from the medical powder storage hole via the outflow air passageway can be further diffused through the medical powder diffusion chamber, and thus the medical powder can flow into the inhalant port in a finely atomized fashion.

According to the invention the air passageway communicating with the medical powder diffusion chamber is formed to open to the medical powder diffusion chamber at an eccentric position with respect to an axis of the medical powder diffusion chamber so that the air passageway extends tangentially with respect to a lateral cross-section of the medical powder diffusion chamber.

In the inhalant medicator as constructed above, when air flow passes through the inflow air passageway and then flows into the medical powder diffusion chamber, the inflow air passageway eccentrically arranged in the tangential direction of the medical powder diffusion chamber produces whirling flow within the medical powder diffusion chamber. Thus, even when granulated medicines; having a strong condensation property or a bad dispersion, are adhered or stuck to each other, it is possible to atomize the granulated medicines by virtue of the whirling flow.

According to the invention the medical powder storage cylindrical member is constructed by a cylindrical portion rotatably fitted into the inner peripheral wall of the cylindrical fit hole and a knob portion provided at the cylindrical portion and operated rotatably with respect to the medicator body, and inflow and outflow outlet ports through which the inflow and outflow air passageways are opened or closed by way of rotary operation of the knob portion.

In the inhalant medicator as constructed above, the inflow and outflow air passageways can be respectively opened or closed by means of the inflow outlet port and the outflow outlet port by rotating the medical powder storage cylindrical member relative to the medicator body while grasping the knob portion.

According to the invention the medical powder storage cylindrical member is constructed by a cylindrical portion axially slidably fitted into the inner peripheral wall of the cylindrical fit hole, a knob portion provided at the cylindrical portion and capable of taking out or putting in with respect to the medicator body, and inflow and outflow outlet ports through which the inflow and outflow air passageways are opened or closed by way of taking-out or putting-in operation of the knob portion.

In the inhalant medicator as constructed above, the inflow and outflow air passageways can be respectively opened or closed through the inflow outlet port and the outflowoutlet port by taking out or putting in the medical powder storage cylindrical member relative to the medicator body, while grasping the knob portion.

According to the invention a stopper means is provided between the medicator body and the medical powder storage cylindrical member for positioning the medical powder storage cylindrical member at a position where the inflow outlet port is communicated with the inflow air passageway and the outflow outlet port is communicated with the outflow air passageway when operating the medical powder storage cylindrical member.

In the inhalant medicator as constructed above, when operating the medical powder storage cylindrical member, the stopper means can position the medical powder storage cylindrical member at the position where the inflow outlet port and the inflow air passageway are communicated with each other and the outflow outlet port and the outflow air passageway are communicated with each other. Thus, it is possible to easily and certainly open or close the inflow and outflow air passageways.

DESCRIPTION OF THE PREFERRED EMBODIMENTS

Figure 1:
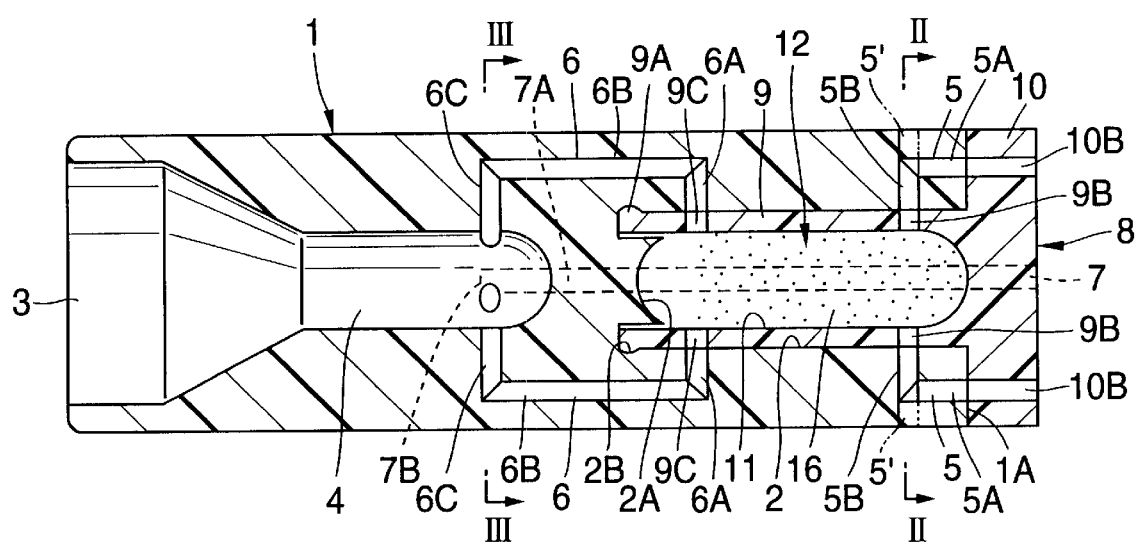
FIG. 1 is a longitudinal cross-sectional view illustrating a first embodiment of an inhalant medicator made according to the invention.

The embodiments of the inhalant medicator of the present invention will be hereinbelow described in detail in reference to the drawings attached hereto.

Referring now to FIGS. 1 through 7, there is shown the first embodiment of the invention. Reference sign 1 denotes a cylindrical medicator body constructing an essential part of the inhalant medicator. The medicator body 1 is formed with a cylindrical fit hole 2 as described later, an inhalant port 3, an inflow air passageway 5, an outflow air passageway 6, and others.

A portion denoted by reference sign 2 is the cylindrical fit hole formed in the medicator body 1 at one axial end. The cylindrical fit hole 2 has an axially extending bore opening at the one axial end face 1A and having a circular shape in cross section and having a bottom. The bottom portion 2A of the cylindrical fit hole is formed as a spherical surface. Also, the bottom portion 2A of the cylindrical fit hole 2 is formed with an annular recessed groove 2B. The annular recessed groove 2B is configured so that an annular protruded portion 9A formed at the tip end portion of a cylindrical portion 9 of a medical powder storage cylindrical member 8, which will be described later.

A portion denoted by reference sign 3 is the inhalant port formed at the other axial end of the medicator body 1. The inhalant port 3 is formed and configured in such a manner as to gradually diametrically enlarged in the other axial direction. Additionally, the inner part of the inhalant port 3 is formed with a medical powder diffusion chamber 4, which will be described later.

A portion denoted by reference sign 4 is the medical powder diffusion chamber located between the cylindrical fit hole 2 and the inhalant port 3 and formed in the medicator body 1. The medical powder diffusion chamber is formed as a cylindrical space axially extending toward the inhalant port 3, so that whirling flow is produced by way of air flow of air flowing through the inflow air passageway which will be described later.

Figure 2:
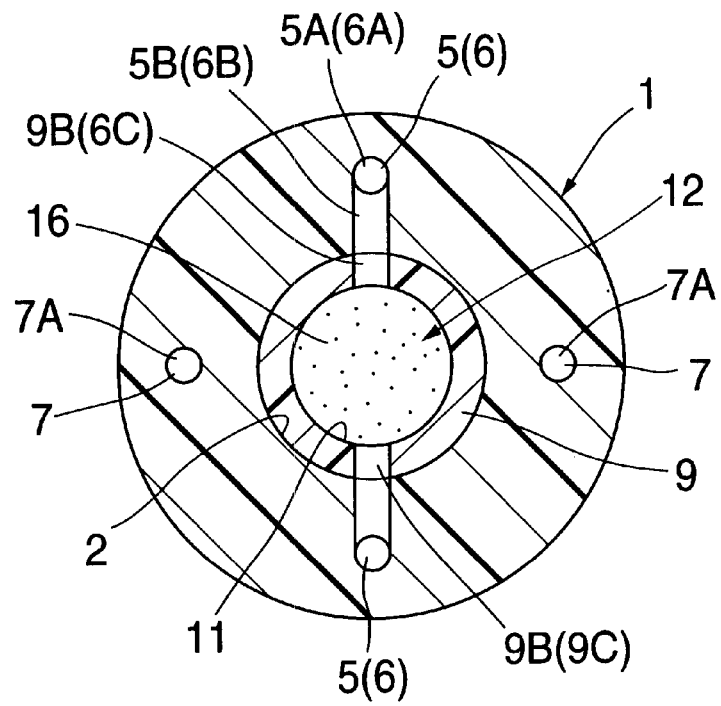
FIG. 2 is an enlarged lateral cross-sectional view illustrating a medicator body, a cylindrical portion, an inflow air passageway (an outflow air passageway), and others as viewed from the arrow indicated by II—II shown in FIG. 1.

Portions denoted by reference signs 5, 5 are two inflow air passageways formed in one axial end of the medicator body 1. As shown in FIGS. 1 and 2, each of the inflow air passageways 5 is constructed by axially-extending axial passages 5A, 5A located on the outer periphery of the cylindrical fit hole 2 and opening to the atmosphere at the one axial end face 1A, and radial passages 5B, 5B communicating the respective axial passages 5A and extending in the radial direction of the medicator body 1 and opening to the cylindrical fit bore 2.

Portions denoted by reference signs 6, 6 are two outflow air passageways formed in a substantially middle portion of the medicator body 1 (as viewed from the axial direction of the medicator body). Each of the outflow air passageways 6 is constructed by radial air passageways 6A, 6A extending in the radial direction of the medicator body 1 and opening to the cylindrical fit hole 2, and axial passages 6B, 6B communicating the respective tip end portions of the radial passages 6A and extending in two opposite axial directions, and diffusion chamber inflow passages 6C, 6C formed as radial passages extending radially from the respective tip end portions of the axial passages 6B and opening to the diffusion chamber 4.

The diffusion chamber inflow passage 6C of the inflow air passageway 6, opening to the medical powder diffusion chamber 4, is formed so that its tip end portion opens at an eccentric position with respect to the axis of the medical powder diffusion chamber 4 so that the diffusion chamber inflow passage 6C extends tangentially with respect to lateral cross section of the medical powder diffusion chamber 4. As a result of this, air flow flowing through the diffusion chamber inflow passage 6C into the medical powder diffusion chamber 4 becomes changed or converted into whirling flow, thus finely atomizing a lump of granular or powdered medicines 16 adhered to each other due to aggregation, condensation or the like.

Figure 3:
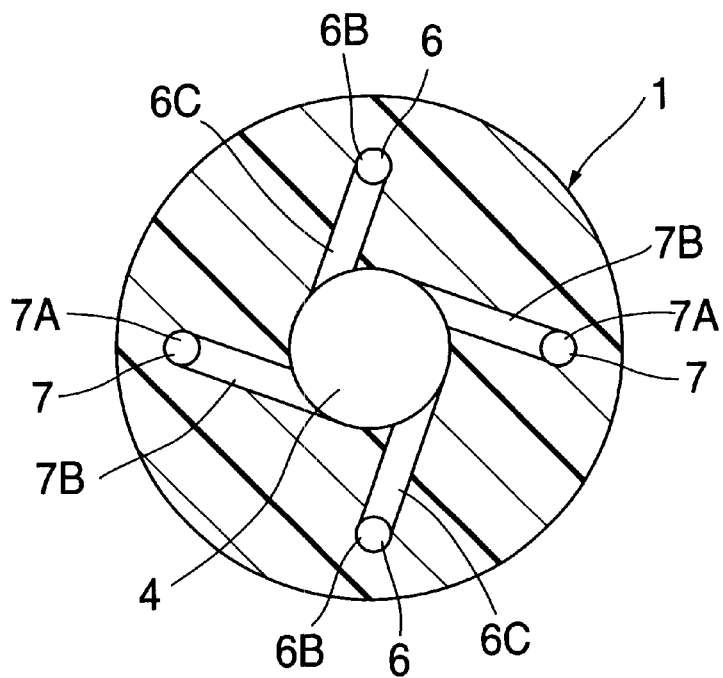
FIG. 3 is an enlarged lateral cross-sectional view illustrating a medicator body, an outflow air passageway, and others as viewed from the arrow indicated by III—III shown in FIG. 1.

Portions denoted by reference signs 7, 7 are two auxiliary air passageways located on the outer periphery of the cylindrical fit hole 2 and formed in the medicator body 1. As shown in FIG. 3, each of the auxiliary air passageways 7 is provided at a position rotated 90 degrees with respect to the respective air passageways 5, 6. The auxiliary air passageway 7 is constructed by axial passages 7A, 7A located on the outer periphery of the cylindrical fit hole 2 and extending in the axial direction and opening to the atmosphere at the one axial end face 1A, and diffusion chamber inflow passages 7B, 7B formed as radial passages communicating the respective axial passages 7A and extending in the radial direction of the medicator body 1 and opening to the medical powder diffusion chamber 4. Each of the auxiliary air passageways 7 functions to avoid difficulty in breathing action by increasing a quantity of air flowing through the medicator during breathing action, and to strengthen the whirling flow within the medical powder diffusion chamber 4.

Hereupon, in the same manner as the diffusion chamber inflow passage 6C of the outflow air passageway 6 described previously, the diffusion chamber inflow passage 7B of the auxiliary air passageway 7 opening to the medical powder diffusion chamber 4 is formed so that its tip end portion opens at an eccentric position with respect to the axis of the medical powder diffusion chamber 4 so that the diffusion chamber inflow passage 6C extends tangentially with respect to a lateral cross section of the medical powder diffusion chamber 4. thus producing the whirling flow within the medical powder diffusion chamber 4 by way of air flow flowing into the medical powder diffusion chamber 4. The whirling flow can finely atomize a lump of granular or powdered medicines 16 adhered to each other due to aggregation, condensation or the like.

Figure 4:
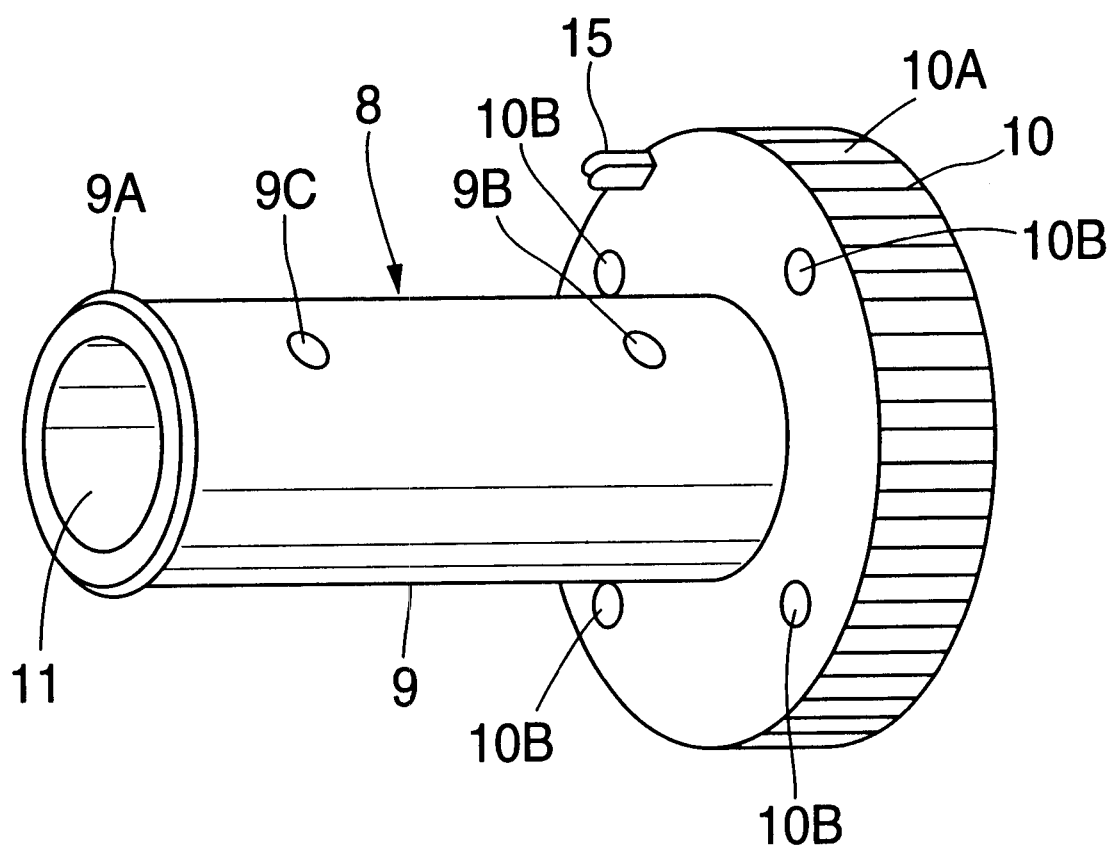
FIG. 4 is an enlarged perspective view illustrating the appearance of a medical powder storage cylindrical member.

Next, a portion denoted by reference sign 8 is a medical powder storage cylindrical member rotatably installed at the opening end of the cylindrical fit hole 2. As shown in FIG. 4, the medical powder storage cylindrical member 8 is mainly constructed by a cylindrical portion 9 inserted and fitted into the cylindrical fit hole 2, and a disc-shaped knob portion 10 provided at the base portion of the cylindrical portion 9. The interior of the cylindrical portion 9 is formed as a medical powder storage hole 11 having a bottom and opening towards its tip end. Hereupon, the above medical powder storage hole 11 defines a medical powder storage chamber 12 capable of storing the medical powder 16 between the storage hole and the bottom portion 2A of the cylindrical fit hole 2 byway of fit of the cylindrical portion 9 into the cylindrical fit hole 2 of the medicator body 1.

Additionally, the previously-noted cylindrical portion 9 is formed at its tip end portion with an annular protruded portion 9A which is fitted into the annular recessed groove 2B of the cylindrical fit hole 2. Fitted engagement between the annular recessed groove 2B and the annular protruded portion 9A prevents the medical powder storage cylindrical member 8 from falling out. Furthermore, the cylindrical portion 9 is formed at a position corresponding to the radial passage 5B of the inflow air passageway 5 in the axial direction with an inflow outlet port 9B so that the inflow outlet port extends or penetrates in the radial direction, and is also formed at a position corresponding to the radial passage 6A of the outflow air passageway 6 in the axial direction with an outflow outlet port 9C so that the outflow outlet port extends or penetrates in the radial direction.

Figure 5:
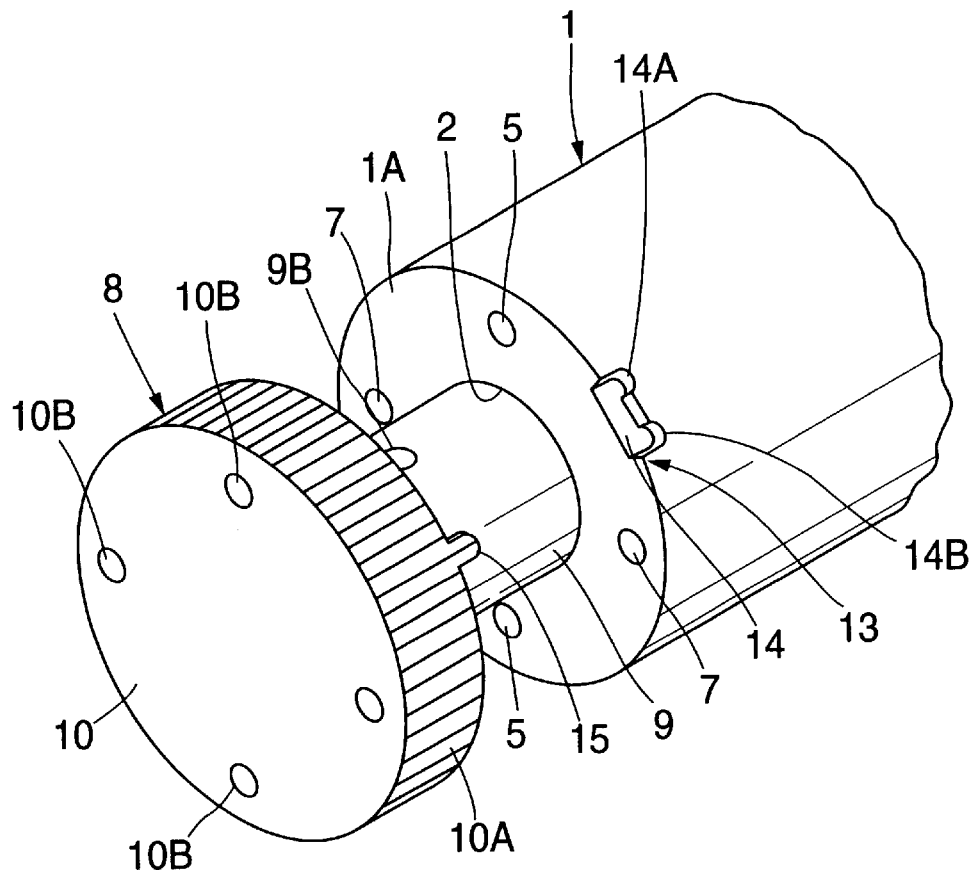
FIG. 5 is an enlarged perspective view illustrating an essential part of a stopper mechanism provided at the medicator body and the knob portion of the medical powder storage cylindrical member.
Figure 6:
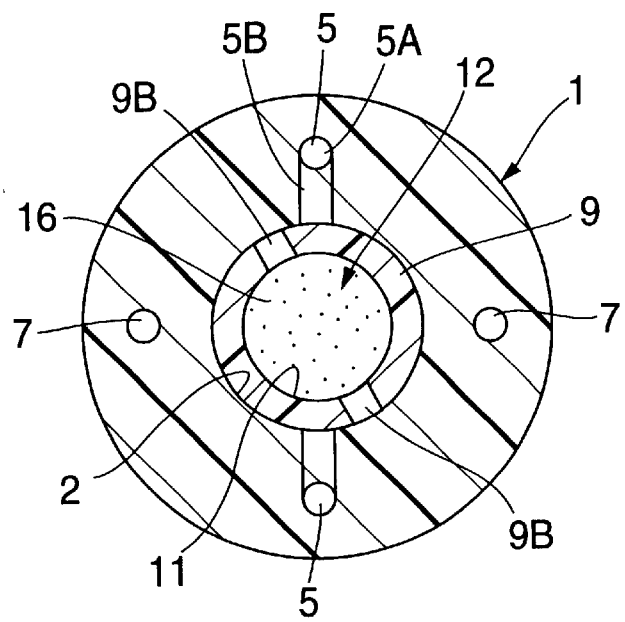
FIG. 6 is an enlarged lateral cross-sectional view illustrating a state of the air passageway formed in the medicator body and the outlet port formed in the cylindrical portion of the medical powder storage cylindrical member, spaced to each other in the circumferential direction, as viewed from the same position as FIG. 2.
Figure 7:
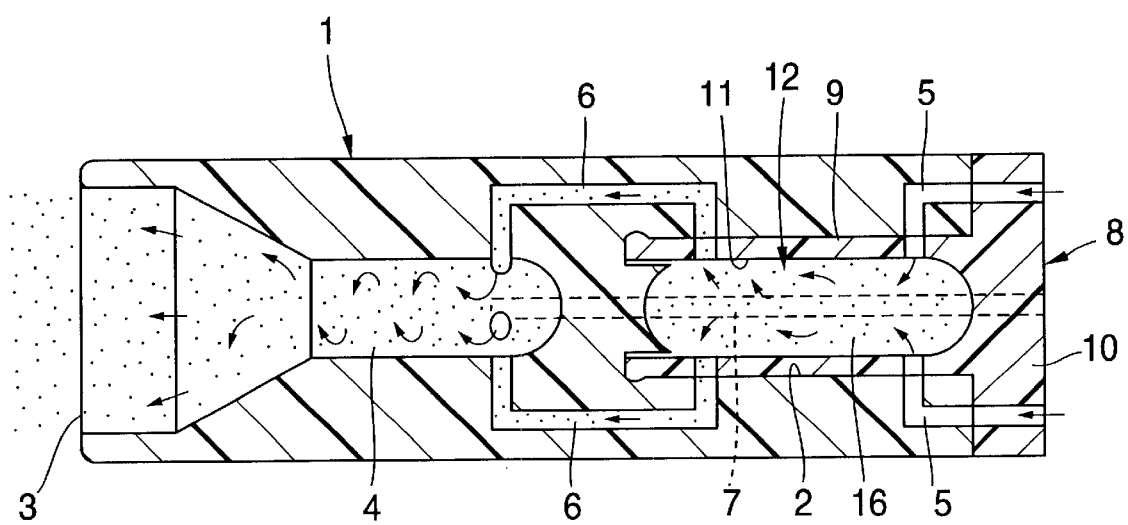
FIG. 7 is a longitudinal cross-sectional view illustrating the inhalant medicator under a particular condition in which medical powders are inhaled, as viewed from the same position as FIG. 1.

On the other hand, the knob portion 10 is abutted-engagement with the one axial end face 1A of the medicator body 1 in a powder-tight fashion. As shown in FIGS. 4 and 5, the knob portion is formed on its outer periphery with a knurling portion 10A serving as a non-slip portion during rotary motion of the medical powder storage cylindrical member 8. Also, the knob portion 10 is formed with atmospheric outlet portions 10B, 10B, . . . at positions corresponding to the outlet ports 9B and 9C of the cylindrical portion 9 in the circumferential direction and also corresponding to the axial passage 5A of the inflow air passageway 5 and the axial passage 7A of the auxiliary air passageway 7 in the radial direction, so that the atmospheric outlet portions extend or penetrate in the axial direction.

The medical powder storage cylindrical member 8 closes the medical powder storage chamber 12 by rotating the cylindrical portion 9 relative to the medicator body 1 while grasping the knob portion 10 and therefore moving the air passageways 5 and 6 and the outlet ports 9B and 9C in the circumferential direction, with the result that the medical powder storage chamber 12 is fully closed. On the other hand, by establishing fluid communication between the air passageway 5 and the outlet port 9B and fluid communication between the air passageway 6 and the outlet port 9C, the air passageways 5 and 6 are opened to the medical powder storage chamber, with the result that inhalation action of the medical powders can be allowed.

At this time, the atmospheric outlet ports 10B formed in the knob portion 10 act to open or close the air passageways 5 and 7. Therefore, under a condition where the air passageways 5 and 7 are closed by means of the knob portion 10, it is possible to prevent dusts from flowing from the outside into the air passageways 5 and 7.

A portion denoted by 13 is a stopper mechanism serving as a stopper means provided between the medicator body 1 and the medical powder storage cylindrical member 8. The stopper mechanism 13 is constructed by a positioning groove 14 formed in the outer periphery of the medicator body 1 and a protruded portion 15 located on the outer periphery of the knob portion 10 of the medical powder cylindrical member 8 and projected toward the positioning groove 14. Also, the positioning groove 14 is formed with a closed-position recessed portion 14A which is brought into engagement with the protruded portion 15 at the closed position (see FIG. 6) at which the inflow air passageway 5 and the inflow outlet port 9B are offset to each other, the outflow air passageway 6 and the outflow outlet port 9C are offset to each other, and the auxiliary air passageway 7 and the atmospheric outlet port 10B are offset to each other, and an open-position recessed portion 14B which is brought into engagement with the protruded portion 15 at the open position (see FIG. 2) where the air passageways 5, 6 and 7 are communicated with the respective outlet ports 9B, 9C, and 10B. As a result of this, the stopper mechanism 13 permits the air passageways 5, 6 and 7 to be easily rapidly communicated with the respective outlet ports 9B, 9C and 10B with the rotary action of the medical powder storage cylindrical member 8 relative to the medicator body 1.

Reference sign 16 denotes medical powder stored in the cylindrical fit hole 2. The medical powder 16 is formed as powdered or granulated medicines. The medical powder 16 is charged into the medical powder storage chamber 12 at a stage where the medical powder storage cylindrical member 8 is installed on the medicator body 1.

The inhalant medicator of the embodiment is constructed as previously discussed. Hereinbelow described in detail are the operation of the inhalant medication through which the patient inhales the medical powder, and the flow of air and medical powder during inhalation.

First, rotary operation of the medical powder storage cylindrical member 8 relative to the medicator body 1 is made, so as to establish fluid communication between the inflow air passageway 5 and the inflow outlet port 9B, fluid communication between the outflow air passageway 6 and the outflow outlet port 9C, and fluid communication between the auxiliary air passageway 7 and the atmospheric outlet port 10B, and thus to ensure the open position.

Next, under this condition, the patient draws his or her breath while taking the inhalant port 3 in his or her mouth. As a result of this, as can be seen from the arrow shown in FIG. 7, air (atmosphere) passes through the atmospheric outlet port 10B of the knob portion 10, the inflow air passageway 5, and the inflow outlet port 9B of the cylindrical portion 9, and then flows into the medical powder storage chamber 12. At this time, air flow flowing into the medical powder storage chamber 12 disperses and atomizes the medical powder 16 stored in the medical powder storage chamber 12.

However, there is a lump of medical powder 16 existing in the internal space. The medical powder 16 passes through the outflow outlet port 9C of the cylindrical portion 9 and the outflow air passageway 6, and then flows into the medical powder diffusion chamber 4. A lump of medical powder 16 can be diffused within the medical powder diffusion chamber 4 by way of whirling flow produced by the diffusion chamber inflow passages 6C and 7B, thus certainly atomizing the medical powder.

In this manner, the medical powder 16, finely atomized within the medical powder diffusion chamber 4, is discharged into the inhalant port 3. Thus, it is possible to prescribe the medical powder via the oral cavity and trachea of a patient into lungs of the patient by inhaling the medical powder discharged via the inhalant port 3 by way of breathing action of the patient.

As discussed above, according to the embodiment, the inhalant medicator can be constructed by two component parts, namely the medicator body 1 and the medical powder storage cylindrical member 8, thus reducing the number of component parts, and ensuring more simplified inhalator structure and reduced production costs, in comparison with the conventional inhalant medicator.

Furthermore, it is possible to open or close the inflow air passageway 5 and the outflow air passageway 6 with respect to the medical powder storage chamber 12 by means of the medical powder storage cylindrical member 8. Thus, it is possible to tightly encapsulate the medical powder 16 within the medical powder storage chamber 12, thus preventing undesirable loss of flow of medical powder 16.

As appreciated from the above, even when the inhalant medicator of the embodiment is thrown away after the inhalant medicator has been used only once, it is possible to reduce an economical burden of the patient. Additionally, even when the medical powder storage chamber 12 is filled with medical powder 16 during assembling process, it is possible to prevent undesirable loss of flow of medical powders 16. Thus, the inhalant medicator of the embodiment can be used as a throwaway type.

On the one hand, the medical powder diffusion chamber 4 is provided between the cylindrical fit hole 2 and the inhalant port 3. Therefore, it is possible to certainly finely atomize the medical powder 16. This ensures an enhanced inhalation efficiency of medical powder 16 and an enhanced reliability of the inhalant medicator. Additionally, it is possible to produce whirling flow within the medical powder diffusion chamber 4, thus more finely atomizing medical powder 16.

Moreover, the stopper mechanism 13 is provided between the medicator body 1 and the medical powder storage cylindrical member 8, for positioning the medical powder storage cylindrical member at either a closed position for prevention of loss of flow of medical powder 16 and an open position for medication, with rotary operation of the medical powder storage cylindrical member 8. Therefore, a series of operations for medication can be easily certainly achieved. Everyone can easily handle the inhalant medicator of the embodiment.

Figure 8:
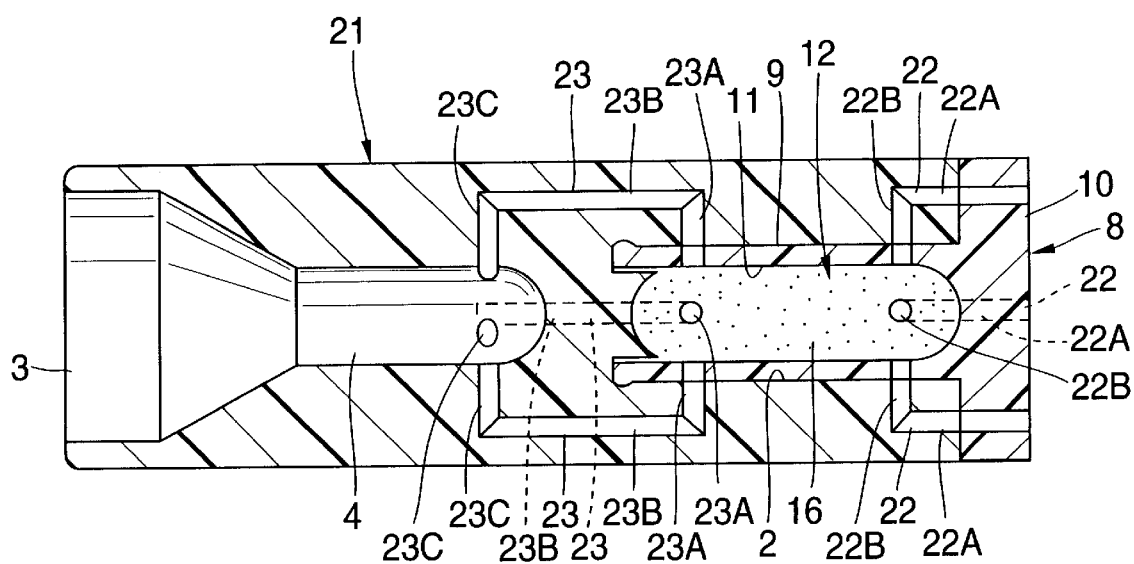
FIG. 8 is a longitudinal cross-sectional view illustrating a second embodiment of an inhalant medicator made according to the invention.
Figure 9:
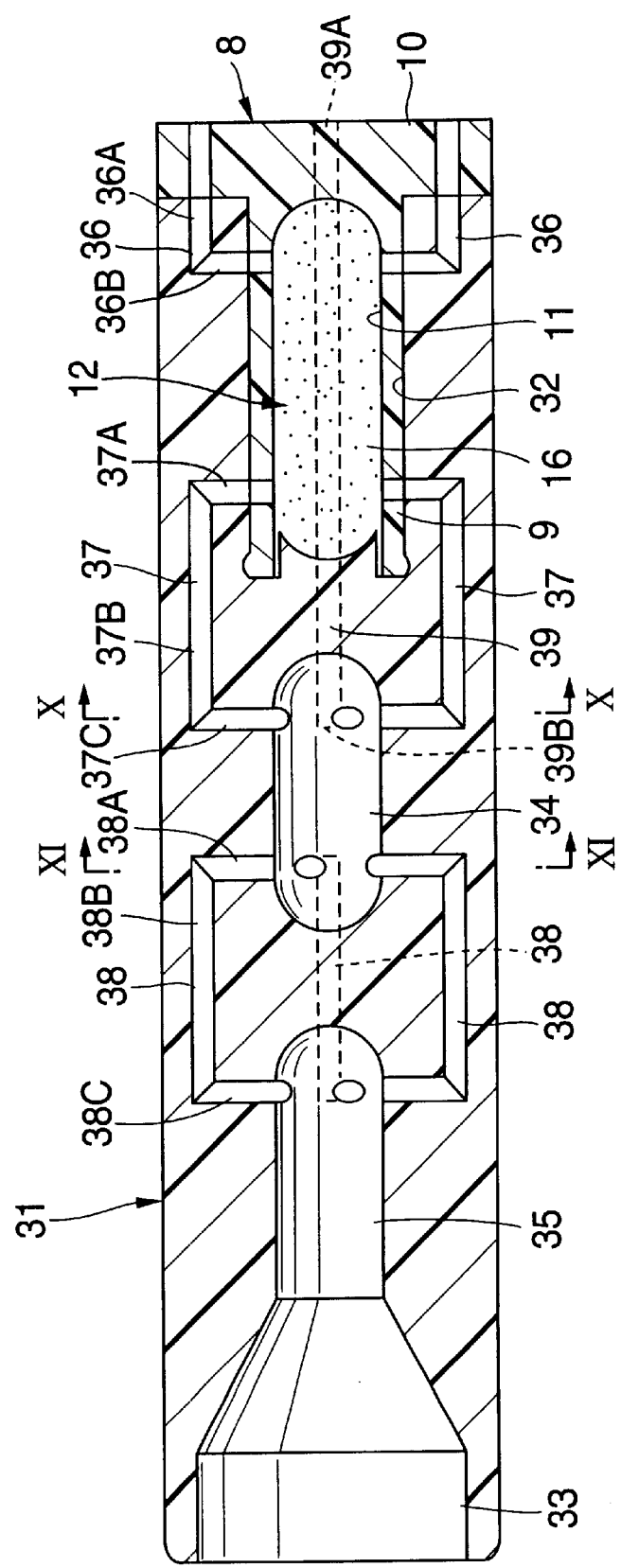
FIG. 9 is a longitudinal cross-sectional view illustrating a third embodiment of an inhalant medicator made according to the invention.
Figure 10:
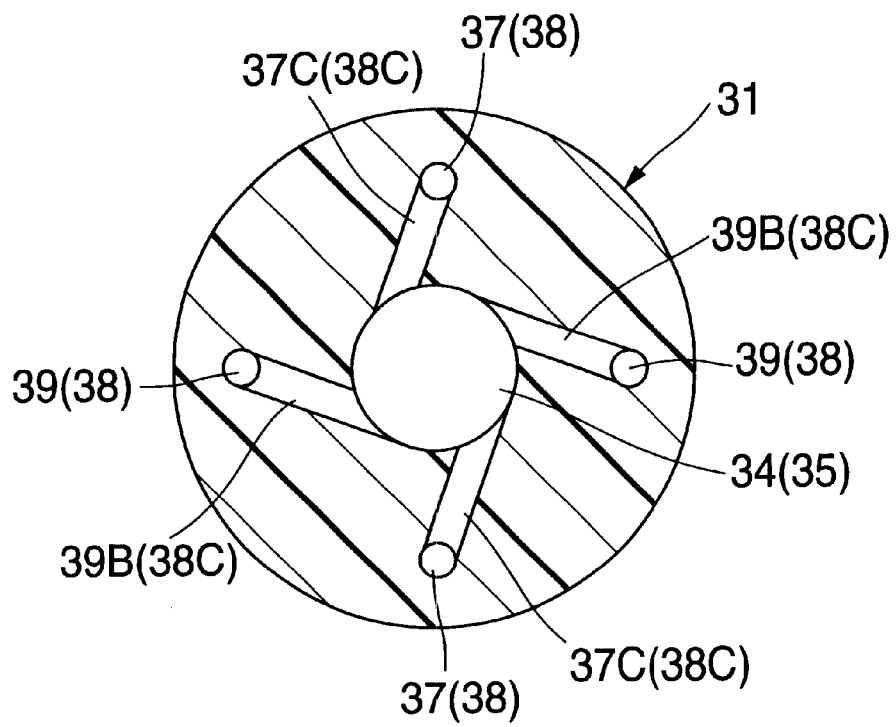
FIG. 10 is an enlarged lateral cross-sectional view illustrating the medicator body, a first outflow air passageway and others, as viewed from the arrow indicated by X—X shown in FIG. 9.

Hereunder described in reference to FIG. 8 is the second embodiment of the invention. In the second embodiment, the auxiliary air passageways used in the first embodiment are eliminated, and in lieu thereof the inflow and outflow air passageways are increased. In the second embodiment, the same reference signs used to designate elements in the first embodiment will be applied to the corresponding elements used in the second embodiment, and detailed description of the same elements will be omitted because the above description thereon seems to be self-explanatory.

A portion denoted by reference sign 21 is a medicator body of the second embodiment. Portions denoted by reference signs 22, 22 . . . are inflow air passageways formed in the medicator body 21. In the same manner as the inflow air passageway 5 of the first embodiment, each of the inflow air passageways 22 is constructed by an axial passage 22A and a radial passage 22B. However, the inflow air passageway 22 of the second embodiment is different from the inflow air passageway 5 of the first embodiment, in that four passageways (only three passageways are shown in the drawing) spaced from each other in the circumferential direction are provided.

Portions denoted by reference signs 23, 23 . . . are outflow air passageways formed in the medicator body 21. In the same manner as the outflow air passageway 6 of the first embodiment, each of the outflow air passageways 23 is constructed by a radial passage 23A, an axial passage 23B, and a diffusion chamber inflow passage 23C. However, the outflow air passageway 23 of the second embodiment is different from the outflow air passageway 6 of the first embodiment, in that four passageways (only three passageways are shown in the drawing) spaced from each other in the circumferential direction are provided.

The second embodiment as constructed above, can provide the same effects and operation as the first embodiment. In particular, in the second embodiment, the auxiliary air passageways 7 used in the first embodiment are eliminated, and in lieu thereof the four inflow air passageways 22 are provided, thus ensuring increased air flow of air flowing into the medical powder storage chamber 12. The increased air flow can effectively atomize the medical powder 16.

Hereinafter described in reference to FIGS. 9 and 12 is the third embodiment of the invention. The third embodiment is characterized in that a second medical powder diffusion chamber is provided between the cylindrical fit hole and the medical powder diffusion chamber. In the third embodiment, the same reference signs used to designate elements in the first embodiment will be applied to the corresponding elements used in the third embodiment, and detailed description of the same elements will be omitted because the above description thereon seems to be self-explanatory.

A portion denoted by reference sign 31 is a medicator body of the third embodiment. Substantially in the same manner as the medicator body 1 of the first embodiment, the medicator body 31 is formed therein with a cylindrical fit hole 32, an inhalant port 33, and others. However, the medicator body 31 of the third embodiment has a first medical powder diffusion chamber 34 and a second medical powder diffusion chamber 35, both provided between the cylindrical fit hole 32 and the inhalant port 33. The medicator body of the third embodiment is different from the medicator body 1 of the first embodiment, in that as a whole the medicator body of the third embodiment is formed as a longer body.

Portions denoted by reference signs 36, 36 . . . are inflow air passageways of the third embodiment. In the same manner as the inflow air passageway 5 of the first embodiment, each of the inflow air passageways 36 is constructed by an axial passage 36A and a radial passage 36B.

Portions denoted by reference signs 37, 37 . . . are two first outflow air passageways. Each of the first outflow air passageways 37 is constructed by radial passages 37A, 37A extending in the radial direction and opening to the cylindrical fit hole 32, axial passages 37B, 37B communicating the respective tip end portions of the radial passages 37A and extending in the axial direction, and diffusion chamber inflow passages 37C, 37C formed as radial passages extending in the radial direction from the respective tip end portions of the axial passages 37B and opening to the first medical powder diffusion chamber 34.

Portions denoted by reference signs 38, 38 . . . are four second outflow air passageways of the third embodiment. Each of the second outflow air passageways 38 is constructed by diffusion chamber outflow passages 38A, 38A formed as radial passages extending in the radial direction and opening to the first medical powder diffusion chamber 34, axial passages 38B, 38B communicating the respective tip end portions of the diffusion chamber outflow passages 38A and extending in the axial direction, and diffusion chamber inflow passages 38C, 38C formed as radial passages extending in the radial direction from the tip end portions of the axial passages 38B and opening to the second medical powder diffusion chamber 35.

Portions denoted by reference signs 39, 39 are two auxiliary air passageways of the third embodiment. Each of the auxiliary air passageways 39 is constructed by axial passages 39A, 39A, and diffusion chamber inflow passages 39B, 39B formed as radial passages communicating the respective axial passages 39A and extending in the radial direction and opening to the first medical powder diffusion chamber 34.

Hereupon, as shown in FIG. 10, the diffusion chamber inflow passage 37C of the first inflow air passageway 37 opening to the first medical powder diffusion chamber 34 and the diffusion chamber inflow passage 39B of the auxiliary air passageway 39 are configured so that their tip end portions open at an eccentric position with respect to the axis of the first medical powder diffusion chamber 34 so that the diffusion chamber inflow passage (37C, 39B) extends tangentially with respect to a lateral cross section of the first medical powder diffusion chamber 34.

Figure 11:
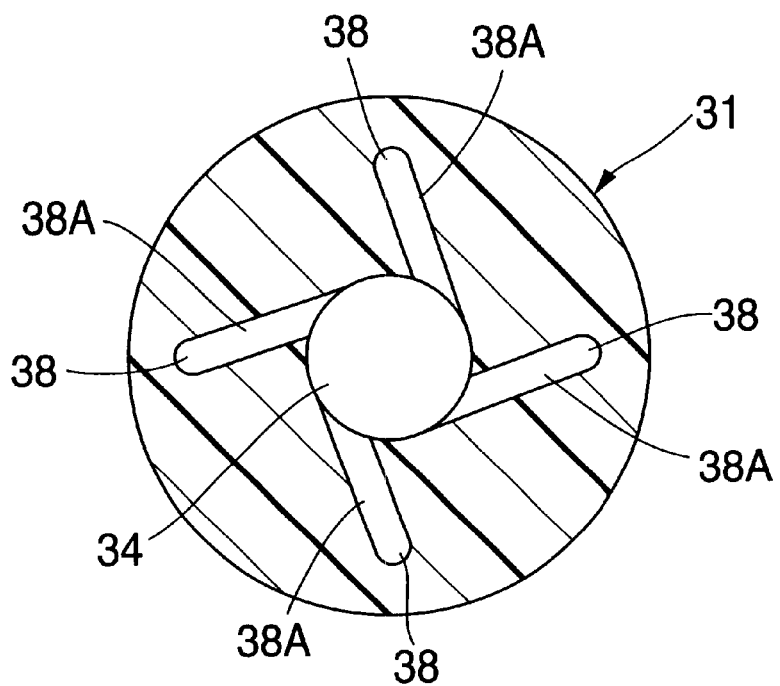
FIG. 11 is an enlarged lateral cross-sectional view illustrating the medicator body, a second outflow air passageway and others, as viewed from the arrow indicated by XI—XI shown in FIG. 9.

As shown in FIG. 11, the diffusion chamber outflow passage 38A of the second outflow air passageway 38 opening to the first medical powder diffusion chamber 34 is configured, so that its tip end portion opens at an eccentric position with respect to the axis of the first medical powder diffusion chamber 34 so that the diffusion chamber outflow passage 38A extends in the tangential direction opposite to the diffusion chamber inflow passage 39B of the auxiliary air passageway 39, in order to facilitate the whirling flow produced within the first medical powder diffusion chamber 34 and passing through the diffusion chamber outflow passage 38A.

Furthermore, the diffusion chamber inflow passage 38C of the second outflow air passageway 38 opening to the second medical powder diffusion chamber 35 opens at an eccentric position with respect to the axis of the second medical powder diffusion chamber 35 so that the diffusion chamber inflow passage 38C extends in the same tangential direction as the diffusion chamber inflow passage 37C of the first outflow air passageway 37 and the diffusion chamber inflow passage 39B of the auxiliary air passageway 39.

Figure 12:
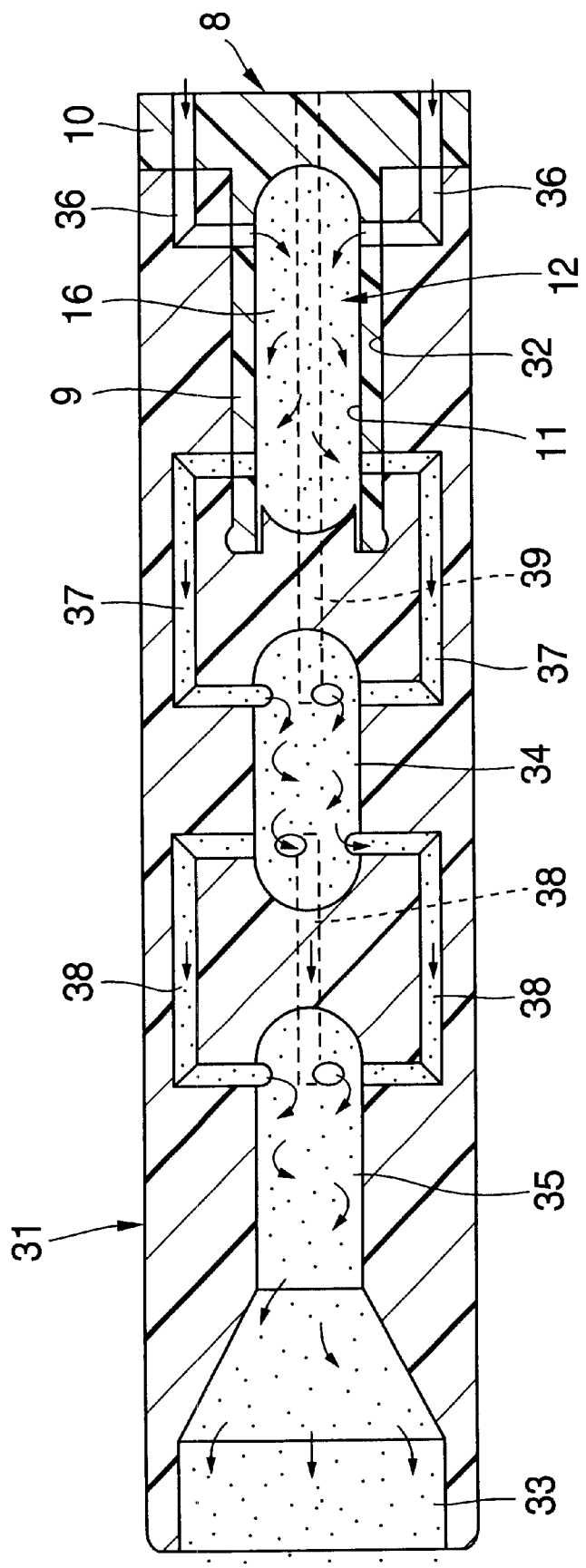
FIG. 12 is a longitudinal cross-sectional view illustrating the inhalant medicator under a particular condition in which a medical powder is inhaled, as viewed from the same position as FIG. 9.

The third embodiment as constructed above, can provide the same effects and operation as the first embodiment. In particular, in the third embodiment, as a granular medicine diffusing chamber, two medical powder diffusion chambers, namely the first and second medical powder diffusion chambers 34 and 35 are provided. Thus, even when the patient draws his or her breath while taking the inhalant port 33 in his or her mouth, under a particular condition where the medical powder 16 includes granulated medicines having a strong condensation property and the granulated medicines are adhered to each other to form a lump of granulated medicines, as can be seen from FIG. 12, it is possible to break and atomize the lump of medical powder by means of the two medical powder diffusion chambers 34 and 35. As a consequence, it is possible to inhale a specified amount of medical powder into lungs of the patient.

Figure 13:
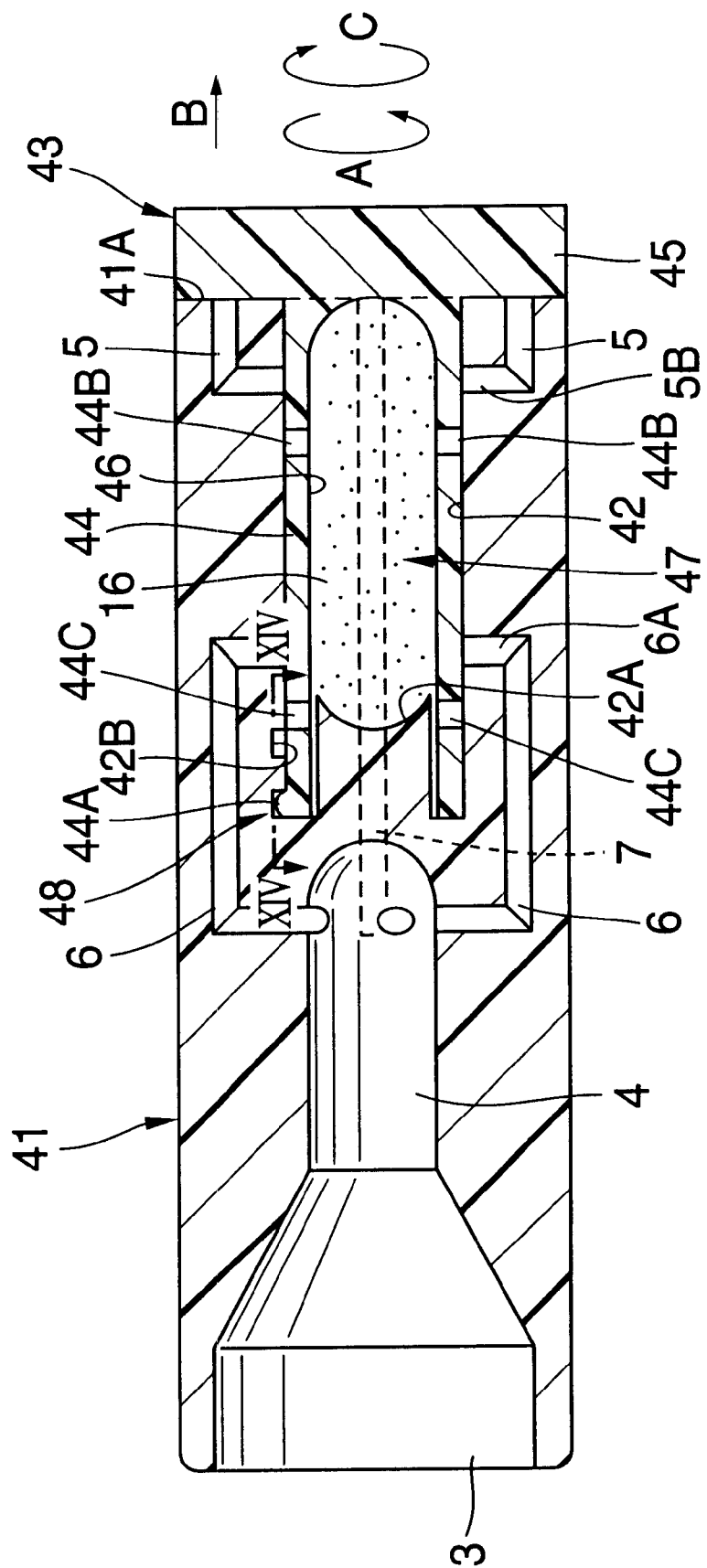
FIG. 13 is a longitudinal cross-sectional view illustrating a fourth embodiment of an inhalant medicator made according to the invention.
Figure 15:
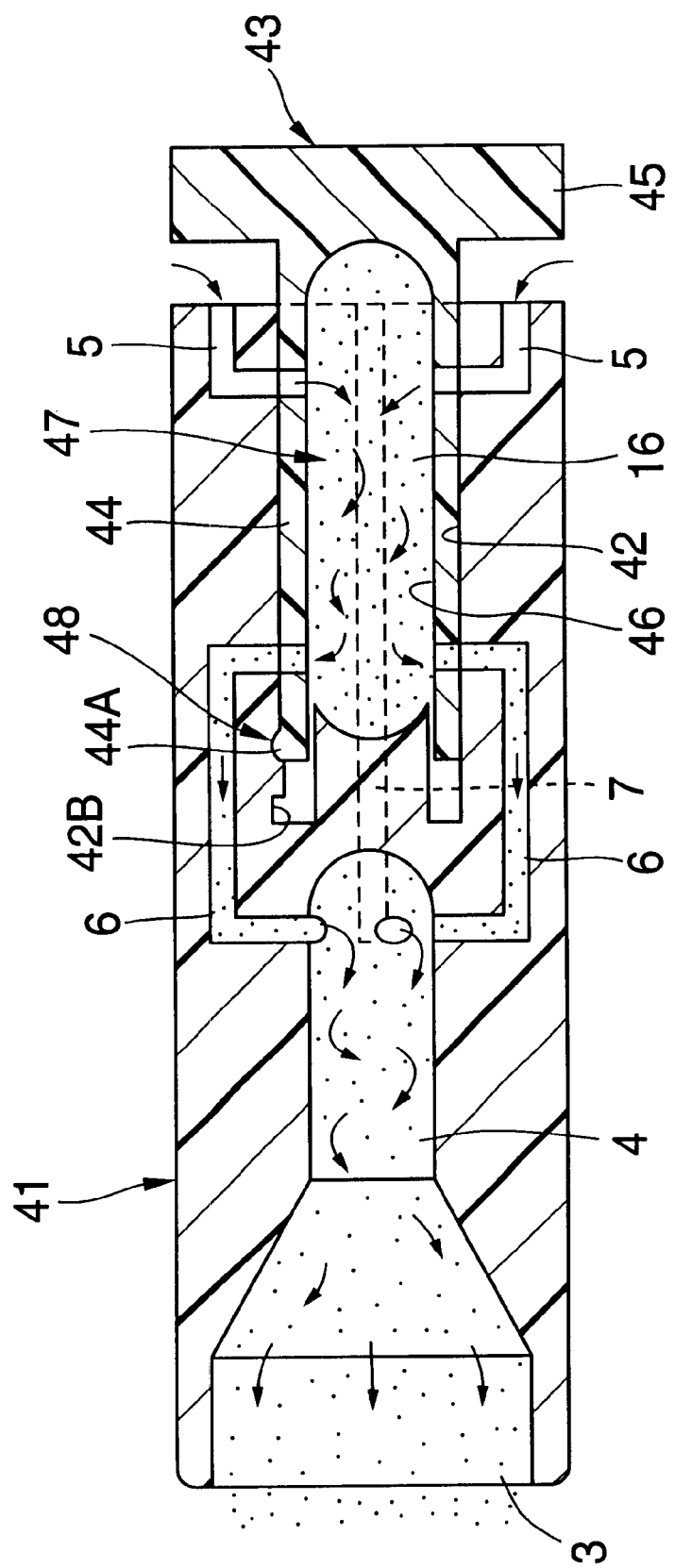
FIG. 15 is a longitudinal cross-sectional view illustrating the inhalant medicator in an inhalation state of medical powder with the medical powder storage cylindrical member extracted from the meditator body, as viewed from the same position as FIG. 13.

Hereinafter described in reference to FIGS. 13 and 15 is the fourth embodiment of the invention. The fourth embodiment is characterized in that a medical powder storage cylindrical member is constructed by a cylindrical portion axially slidably fitted into the inner peripheral surface of the cylindrical fit hole, a knob portion provided at the cylindrical portion and capable of taking out or putting in with respect to the medicator body, and inflow and outflow outlet ports through which the inflow and outflow air passageways are opened or closed by way of taking-out or putting-in operation of the knob portion. In the fourth embodiment, the same reference signs used to designate elements in the first embodiment will be applied to the corresponding elements used in the fourth embodiment, and detailed description of the same elements will be omitted because the above description thereon seems to be self-explanatory.

Figure 14:
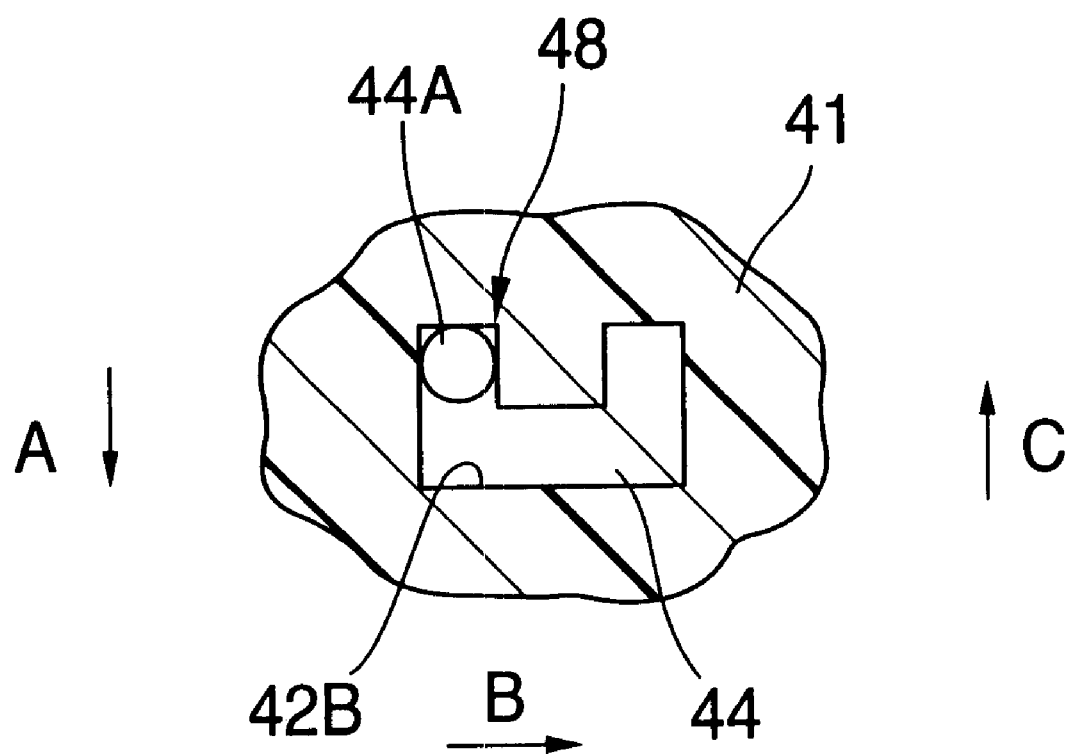
FIG. 14 is an enlarged cross-sectional view illustrating an essential part of the inhalant medicator in an engaged state between a C-shaped groove of the cylindrical fit hole and an engaged protruded portion of the medical powder storage cylindrical member, as viewed from the arrow indicated by XIV—XIV shown in FIG. 9.

A portion denoted by reference sign 41 is a medicator body of the fourth embodiment. A portion denoted by reference sign 42 is a cylindrical fit hole formed in the medicator body 41. The cylindrical fit hole 42 has an axially extending bore opening at one axial end 41A and having a circular shape in cross section and having a bottom. The bottom portion 42A of the cylindrical fit hole is formed as a spherical surface. Also, the bottom portion 42A of the cylindrical fit hole 42 is formed with a C-shaped groove 42B. As shown in FIG. 14, the C-shaped groove 42B is configured in such a manner as to guide movably an engaged protruded portion 44A of a cylindrical portion 44 described later.

A portion denoted by reference sign 43 is a medical powder storage cylindrical member of the fourth embodiment, installed on the cylindrical fit hole 42 so that the medical powder storage cylindrical member is capable of taking out or putting in with respect to the opening end of the cylindrical fit hole 42. Substantially in the same manner as the medical powder storage cylindrical member 8 of the first embodiment, the medical powder storage cylindrical member 43 is mainly constructed by a cylindrical portion 44 inserted and fitted into the cylindrical fit hole 42, and a disc-shaped knob portion 45 provided at the base portion of the cylindrical portion 44. The interior of the cylindrical portion 44 is formed as a medical powder storage hole 46. A medical powder storage chamber 47 is defined between the medical powder storage hole 46 and the bottom portion 42A of the cylindrical fit hole 42.

However, the medical powder storage cylindrical member 43 of the fourth embodiment is different from the medical powder storage cylindrical member 43 of the first embodiment, in that the engaged protruded portion 4A, fitted to the C-shaped groove 42B of the cylindrical fit hole 42, is provided at the tip end portion of the cylindrical portion 44, inflow outlet port 44B and outflow outlet port 44C are formed in the cylindrical portion 44 at positions at which the inflow and outflow outlet ports respectively communicate the radial passage 5B of the inflow air passageway 5 and the radial passage 6A of the outflow air passageway 6 under a condition where the cylindrical portion 44 is extracted, and the atmospheric outlet ports used in the first embodiment are removed from the knob portion 45.

Hereupon, the C-shaped groove 42B formed in the cylindrical fit hole 42 of the medicator body 41 and the engaged protruded portion 44A formed in the cylindrical portion 44 of the medical powder storage cylindrical member 43 cooperate to each other to construct a stopper mechanism 48 serving as a stopper means for positioning the medical powder storage cylindrical member 43 during taking-out/putting-in operation of the medical powder storage cylindrical member 43 with respect to the medicator body 41.

The inhalant medicator of the fourth embodiment is constructed as previously discussed. Hereinbelow described in detail is the operation of the inhalant medication through which the patient inhales the medical powder.

In a state of the medicator prior to inhalant medication, as shown in FIG. 13, the air passageways 5 and 6 are closed by means of the cylindrical portion 44, while the atmospheric side of each of the air passageways 5 and 7 is closed by means of the knob portion 45.

Under this condition, when the inhalant medication has to be made, the medical powder storage cylindrical member 43 is rotated relative to the medicator body 41 in the direction indicated by the arrow A shown in FIGS. 13 and 14. Next, the cylindrical portion 44 of the medical powder storage cylindrical member 43 is extracted in the direction indicated by the arrow B. Thereafter, with rotary motion of the medical powder storage cylindrical member 43, returning the medical powder storage cylindrical member 43 to the direction indicated by the arrow C, as shown in. FIG. 15, it is possible to position in such a manner as to establish fluid communication between the air passageway 5 and the inflow outlet port 44B and fluid communication between the air passageway 6 and the outflow outlet port 44C. Under this condition, when the patient draws his or her breath while taking the inhalant port 3 in his or her mouth, the medical powder 16 can be inhaled.

The fourth embodiment as constructed above, can provide the same effects and operation as the first embodiment.

Figure 16:
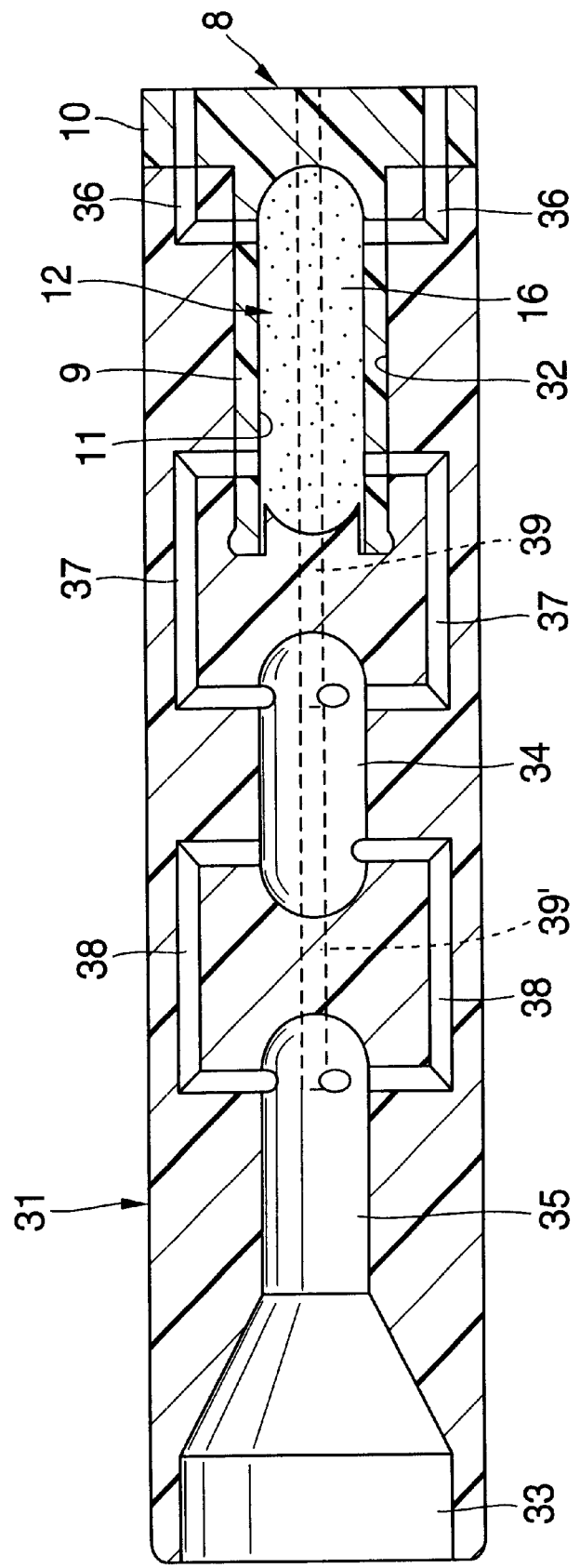
FIG. 16 is a longitudinal cross-sectional view illustrating an inhalant medicator corresponding to a first modification of the invention.

As described above, in the third embodiment, the auxiliary air passageways 39, 39 through which the first medical powder diffusion chamber is communicated with the atmospheric side, is formed in the medicator body 31. However, the present invention is not limited to the particular embodiments shown and described herein. For instance, as can be seen from the first modification shown in FIG. 16, another auxiliary air passageways 39, 39 (only one passageway is shown in the drawing) intercommunicating the atmospheric side and the second medical powder diffusion chamber 35, may be formed in the medicator body 31, independently of the auxiliary air passageways 39, 39 intercommunicating the atmospheric side and the first medical powder diffusion chamber 34.

Additionally, in the first embodiment, the inflow air passageway 5 is constructed by an axial passage 5A and the radial passage 5B. In lieu thereof, as indicated by the two-dotted line shown in FIG. 1, an inflow air passageway 5' may be formed so that the inflow air passageway extends in the radial direction and opens to a curved surface of the medicator body 1. In the same manner, such a construction can be applied to the other embodiments.

Additionally, in the first, second, and fourth embodiments one medical powder diffusion chamber 4 is provided, whereas in the second embodiment and the modification two medical powder diffusion chambers 34, 35 are provided. However, the invention is not limited to the particular embodiments shown and described herein. Alternatively, three or more medical powder diffusion chambers may be provided. It is preferable that the number of the medical powder diffusion chambers is determined or set depending on characteristics or properties of medical powder (such as a condensation property).

On the other hand, as discussed above, in the first embodiment, the medical powder 16 is encapsulated within the cylindrical fit hole 2 at a time when the medicator body 1 and the medical powder storage cylindrical member 8 are assembled to each other. In lieu thereof, the medical powder 16 may be charged into the cylindrical fit hole 2 just before the operation of inhalant medication. In the same manner, such a construction can be applied to the other embodiments.

Additionally, in each of the embodiments, the opening and closing of the inflow air passageways 5, 22, 36 with respect to the atmospheric side are made by the respective knob portions 10, 45 of the medical powder storage cylindrical members 8, 43. The invention is not limited to the particular embodiments shown and described herein. For instance, the knob portion is configured to have the same diameter dimension as the cylindrical portion. That is, it is unnecessary to always close the atmospheric outlet port of the inflow air passageway.

Additionally, in each of the embodiments, the inflow air passageways 5, 22, 36 and the outflow air passageways 6, 23, 37 are formed so that these passageways extend in the radial direction towards the central portion of the cylindrical fit holes 2, 32, 42. In lieu thereof, these air passageways may be constructed so that the air passageways open to the respective cylindrical fit holes at eccentric positions in which the air passageways extend in the respective tangential directions of the cylindrical fit holes.

Figure 17:
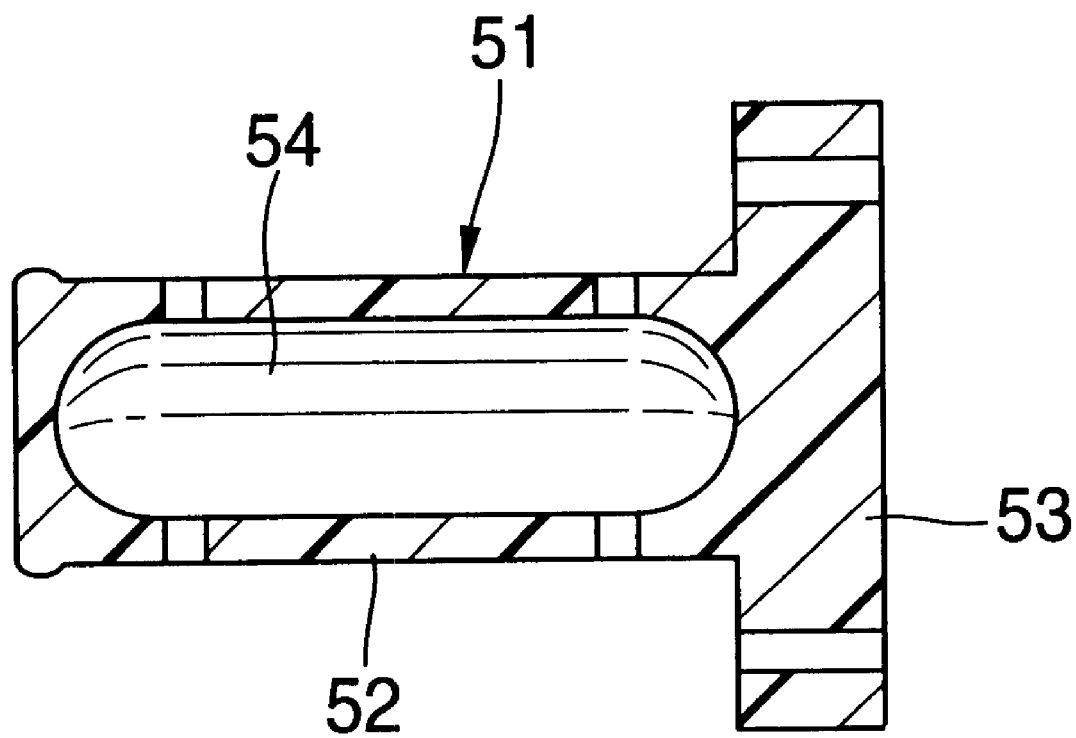
FIG. 17 is a longitudinal cross-sectional view illustrating only a medical powder storage cylindrical member corresponding to a second modification of the invention.

Furthermore, in the first embodiment, the medical powder storage chamber 12 is defined between the bottom portion 2A of the cylindrical fit hole 2 and the medical powder storage hole 11 by fitting the cylindrical portion 9 of the medical powder storage member 8 into the cylindrical fit hole 2 of the medicator body 1. The invention is not limited to the particular embodiments shown and described herein. For instance, as can be seen from the second modification shown in FIG. 17, a medical powder storage hole 54 may be provided by defining the medical powder storage chamber by way of only a cylindrical portion 52 of a medical powder storage cylindrical member 51. In this case, it is preferable that the bottom face of the cylindrical fit hole of the medicator body is designed to be flat. In the same manner, such a construction can be applied to the other embodiments.

As explained above, according to the invention as claimed in claim 1, under a condition where the inflow air passageway and the outflow air passageway are closed with respect to the medical powder storage hole by means of the medical powder storage cylindrical member, it is possible to prevent the medical powder stored in the medical powder storage hole from flowing to the outside via the air passageways. Also, when the medical powder has to be inhaled, the inflow air passageway and the outflow air passageway are opened to the medical powder storage hole by operating the medical powder storage cylindrical member. Under these conditions, the patient draws his or her breath while taking the inhalant port in his or her mouth, atmosphere flown into the inflow air passageway flows into the cylindrical fit hole, taking the form of air flow. As a result of this, the medical powder in the cylindrical fit hole can be atomized. Thus, in a blended condition of the medical powder with air flow, the mixture of the incoming air and medical powder passes through the outflow air passageway and then flows towards within the inhalant port, and thus the patient can inhale the medical powder through the inhalant port into lungs of the patient.

Additionally, the inhalant medicator of the invention is constructed by two component parts, namely the medicator body and the medical powder storage cylindrical member, and also it is possible to open and close each of the air passageways with respect to the medical powder storage hole by means of the medical powder storage cylindrical member, thereby reducing production costs, and consequently ensuring reduced economical burden of the patient. In addition, even when the medical powder storage hole is filled with medical powder in advance, it is possible to prevent the medical powder stored in the medical powder storage hole from flowing to the outside. Thus, the inhalant medicator of the invention can be suitably used as a throwaway type.

According to the invention as claimed in claim 2, the patient can inhale a specified amount of medical powder into lungs. This enhances medical benefits of the powdered or granular medicines, and also enhances the reliability of the inhalant medicator.

According to the invention as claimed in claim 3, it is possible to produce or create whirling flow within the medical powder diffusion chamber by virtue of air flow passing through the air passageway and then flowing into the medical powder diffusion chamber. Even when the medical powder includes granulated medicines having a strong condensation property, it is possible to effectively diffuse and atomize the medical powder by way of the whirling flow, thus more remarkably enhancing an inhalation efficiency of the medical powder.

According to the invention as claimed in claims 4, 5, or 6 the inflow and outflow air passageways can be respectively opened or closed by means of the inflow outlet port and the outflow outlet port by rotating the medical powder storage cylindrical member relative to the medicator body while grasping the knob portion. Thus, under a condition where the inflow air passageway and the outflow air passageway are respectively closed by the inflow outlet port and the outflow outlet port, it is possible to prevent the medical powder to flow out.

According to the invention as claimed in claims 7, 8, or 9 the inflow and outflow air passageways can be respectively opened or closed through the inflow outlet port and the outflow outlet port by taking out or putting in the medical powder storage cylindrical member relative to the medicator body, while grasping the knob portion. Thus, under a condition where the inflow air passageway and the outflow air passageway are respectively closed by the inflow outlet port and the outflow outlet port, it is possible to prevent the medical powder to flow out.

According to the invention as claimed in claim 10 or 11 when operating the medical powder storage cylindrical member, the stopper means can position the medical powder storage cylindrical member at the position where the inflow outlet port and the inflow air passageway are communicated with each other and the outflow outlet port and the outflow air passageway are communicated with each other. Thus, it is possible to easily and certainly open or close the inflow and outflow air passageways, thus ensuring enhanced operability or easy manipulation.

What is claimed is:

1. An inhalant medicator comprising:

a medicator body formed with a cylindrical fit hole opening at one axial end and formed at the other axial end with an inhalant port;

an inflow air passageway formed in the medicator body for supplying air into the cylindrical fit hole;

an outflow air passageway formed in the medicator body for discharging air from the cylindrical fit hole into the inhalant port; and a medical powder storage cylindrical member fit to the cylindrical fit hole of the medicator body and having a cylindrical portion defining therein a medical powder storage hole whose internal space stores a medical powder, wherein a portion of the inflow air passageway and a portion of the outflow air passageway are formed in the medical powder storage cylindrical member, and the portions of the inflow air passageway and the outflow air passageway act to establish and block fluid communication between the inflow and outflow air passageways formed in the medicator body and the medical powder storage hole by movement of the medical powder storage cylindrical member relative to the medicator body.

2. The inhalant medicator as claimed in claim 1, wherein at least one medical powder diffusion chamber is formed in the medicator body and located between the cylindrical fit hole and the inhalant port for diffusing the medical powder flowing out of the outflow air passageway.

3. The inhalant medicator as claimed in claim 2, wherein an air passageway portion of the outflow air passageway communicating with the medical powder diffusion chamber is formed to open to the medical powder diffusion chamber at an eccentric position with respect to an axis of the medical powder diffusion chamber so that the air passageway extends tangentially with respect to a cross section of the medical powder diffusion chamber.

4. The inhalant medicator as claimed in claim 1, wherein the medical powder storage cylindrical member comprises a cylindrical portion rotatably fitted into an inner peripheral wall of the cylindrical fit hole and a knob portion provided at the cylindrical portion and operated rotatably with respect to the medicator body, and inflow and outflow outlet ports through which the inflow and outflow air passageways are opened or closed by way of rotary operation of the knob portion.

5. The inhalant medicator as claimed in claim 2, wherein the medical powder storage cylindrical member comprises a cylindrical portion rotatably fitted into an inner peripheral wall of the cylindrical fit hole and a knob portion provided at the cylindrical portion and operated rotatably with respect to the medicator body, and inflow and outflow outlet ports through which the inflow and outflow air passageways are opened or closed by way of rotary operation of the knob portion.

6. The inhalant medicator as claimed in claim 3, wherein the medical powder storage cylindrical member comprises a cylindrical portion rotatably fitted into an inner peripheral wall of the cylindrical fit hole and a knob portion provided at the cylindrical portion and operated rotatably with respect to the medicator body, and inflow and outflow outlet ports through which the inflow and outflow air passageways are opened or closed by way of rotary operation of the knob portion.

7. The inhalant medicator as claimed in claim 1, wherein the medical powder storage cylindrical member comprises a cylindrical portion axially slidably fitted into an inner peripheral wall of the cylindrical fit hole, a knob portion provided at the cylindrical portion and capable of taking our or putting in with respect to the medicator body, and inflow and outflow outlet ports through which the inflow and outflow air passageways are opened or closed by way of taking-out or putting-in operation of the knob portion.

8. The inhalant medicator as claimed in claim 2, wherein the medical powder storage cylindrical member comprises a cylindrical portion axially slidably fitted into an inner peripheral wall of the cylindrical fit hole, a knob portion provided at the cylindrical portion and capable of taking our or putting in with respect to the medicator body, and inflow and outflow outlet ports through which the inflow and outflow air passageways are opened or closed by way of taking-out or putting-in operation of the knob portion.

9. The inhalant medicator as claimed in claim 3, wherein the medical powder storage cylindrical member comprises a cylindrical portion axially slidably fitted into an inner peripheral wall of the cylindrical fit hole, a knob portion provided at the cylindrical portion and capable of taking our or putting in with respect to the medicator body, and inflow and outflow outlet ports through which the inflow and outflow air passageways are opened or closed by way of taking-out or putting-in operation of the knob portion.

10. The inhalant medicator as claimed in claim 4, wherein a stopper means is provided between the medicator body and the medical powder storage cylindrical member for positioning the medical powder storage cylindrical member at a position where the inflow outlet port is communicated with the inflow air passageway and the outflow outlet port is communicated with the outflow air passageway when operating the medical powder storage cylindrical member.

11. The inhalant medicator as claimed in claim 7, wherein a stopper means is provided between the medicator body and the medical powder storage cylindrical member for positioning the medical powder storage cylindrical member at a position where the inflow outlet port is communicated with the inflow air passageway and the outflow outlet port is communicated with the outflow air passageway when operating the medical powder storage cylindrical member.

* * * * *